United States Patent [19]
Garrison et al.

[11] Patent Number: 4,810,331
[45] Date of Patent: Mar. 7, 1989

[54] SURFACTANT SENSING ELECTRODE FOR POTENTIOMETRIC TITRATIONS

[75] Inventors: Robert A. Garrison, Southlake, Tex.; Martin A. Phillippi, Pleasanton, Calif.

[73] Assignee: The Clorox Company, Oakland, Calif.

[21] Appl. No.: 108,196

[22] Filed: Oct. 13, 1987

[51] Int. Cl.$^4$ ............................................. G01N 27/46
[52] U.S. Cl. .................................. 204/1 T; 204/405; 204/418; 422/75
[58] Field of Search .............................. 204/416–419, 204/405, 1 T, 1 M, 1 K; 422/75–77

[56] References Cited

U.S. PATENT DOCUMENTS

| | | | |
|---|---|---|---|
| 3,446,726 | 5/1969 | Pungor et al. | 204/296 |
| 3,562,129 | 2/1971 | Simon | 204/195 |
| 3,562,139 | 8/1971 | Leitz | 204/296 |
| 3,691,047 | 9/1972 | Ross et al. | 204/195 |
| 3,753,887 | 8/1973 | Kedem et al. | 204/195 |
| 3,835,011 | 9/1974 | Baum et al. | 204/195 M |
| 3,840,452 | 10/1974 | Baum et al. | 204/195 M |
| 3,843,490 | 10/1974 | Higuchi | 204/1 T |
| 3,856,649 | 12/1974 | Genshaw et al. | 204/195 F |
| 3,932,233 | 1/1976 | Ruzicka et al. | 204/195 M |
| 4,115,209 | 9/1978 | Freiser et al. | 204/1 T |
| 4,214,968 | 7/1980 | Battagalia et al. | 204/195 M |
| 4,233,136 | 11/1980 | Spaziani et al. | 204/195 L |
| 4,236,987 | 12/1980 | Schindler et al. | 204/195 M |
| 4,242,191 | 12/1980 | Schindler et al. | 204/195 M |
| 4,314,895 | 2/1982 | Spaziani et al. | 204/195 M |
| 4,361,473 | 11/1982 | Young et al. | 204/195 M |
| 4,379,041 | 4/1983 | Petranek et al. | 204/415 |
| 4,399,002 | 8/1983 | Freiser et al. | 204/1 T |
| 4,519,891 | 5/1985 | Sugahara et al. | 204/418 |
| 4,597,848 | 7/1986 | Oka et al. | 204/418 |

FOREIGN PATENT DOCUMENTS

| | | |
|---|---|---|
| 569981 | 12/1984 | Czechoslovakia . |
| 201240 | 5/1985 | Japan . |
| 8500494 | 5/1986 | PCT Int'l Appl. . |
| 1078325 | 3/1984 | U.S.S.R. . |

OTHER PUBLICATIONS

RC24222, 09/19/56, Patnode et al.
Reid et al. "Determination of . . . Detergents by Two-Phase Titration" *Comm. Int'l d'Analyses,* Milan (1966).
Holness et al., "A Systematic Scheme of Semi-Micro Quantitative Analysis . . . ", *Analyst,* vol. 82 (1957).
Goina et al., "Potentiometric Titration . . . Using Liquid Membrane Selective Ion Electrodes", *Sosit la Redactie,* (Apr. 1982).
Rippin et al. "PVC-Surfactant-Selective Electrode Responsive to Primary Amines", *Colloids and Surfaces,* vol. 15 (1985).
Gulevich et al. "Film Ionselective Alkylsulfate Electrodes . . .", *Jour Anal. Chem* vol. XL (9) (1985).
Jones et al. "Barium-Polyethoxylate Complex as Potentiometric Sensors . . .", *Analyst,* vol. 106 (Sep. 1981).
Xixing et al., "Preparation and Application of Polyethoxylate . . . Electrodes", Shanghai Instut Org. Chem (1985).
Cutter et al. "Surfactant-Sensitive Polymeric Membrane Electrodes", *J. Electroanal. Chem* vol. 85(1) (1977).
Dilley "Determination of Anionic-Active Matter . . . by Potentiometric Titration", *Analyst,* vol. 105, (1980).
Cunningham et al., "Coated-Wire Ion-Selective Electrodes", *Analytica Chimica Acta,* vol. 180 (1986).

*Primary Examiner*—T. Tung
*Attorney, Agent, or Firm*—Michael J. Mazza; Joel J. Hayashida; Stephen M. Westbrook

[57] ABSTRACT

A coated-wire electrode for potentiometrically titrating surfactant molecules having more than ten carbon atoms includes an electrically-conductive core coated with a semipermeable membrane. The membrane matrix includes a polymer a plasticizer and an ion-exchanger material consisting essentially of dimidium bromide-disulphine blue in suitable proportions to be surfactant selective. The membrane is responsive to anionic, cationic and amphoteric surfactants as well as alkoxylated nonionic surfactants.

21 Claims, 4 Drawing Sheets

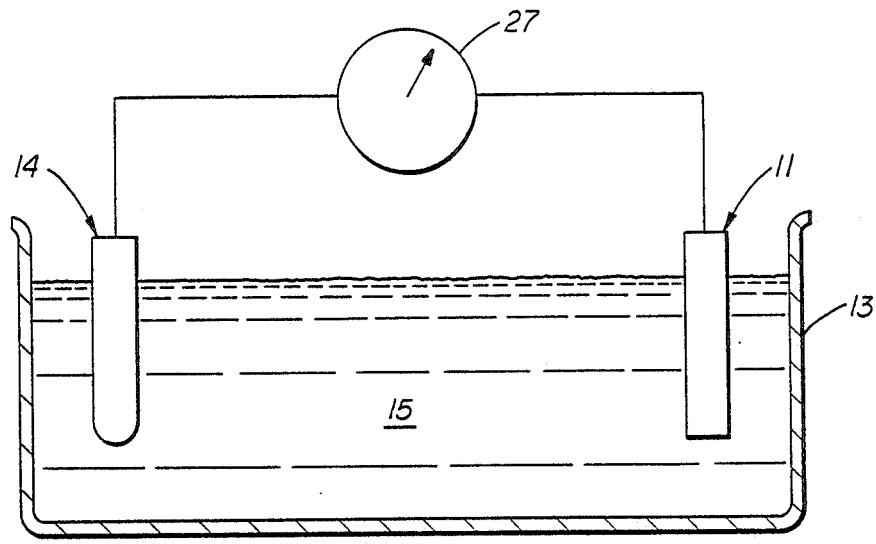
FIG._1.
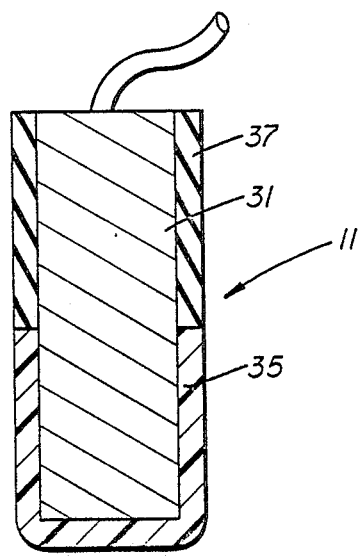
FIG._2.

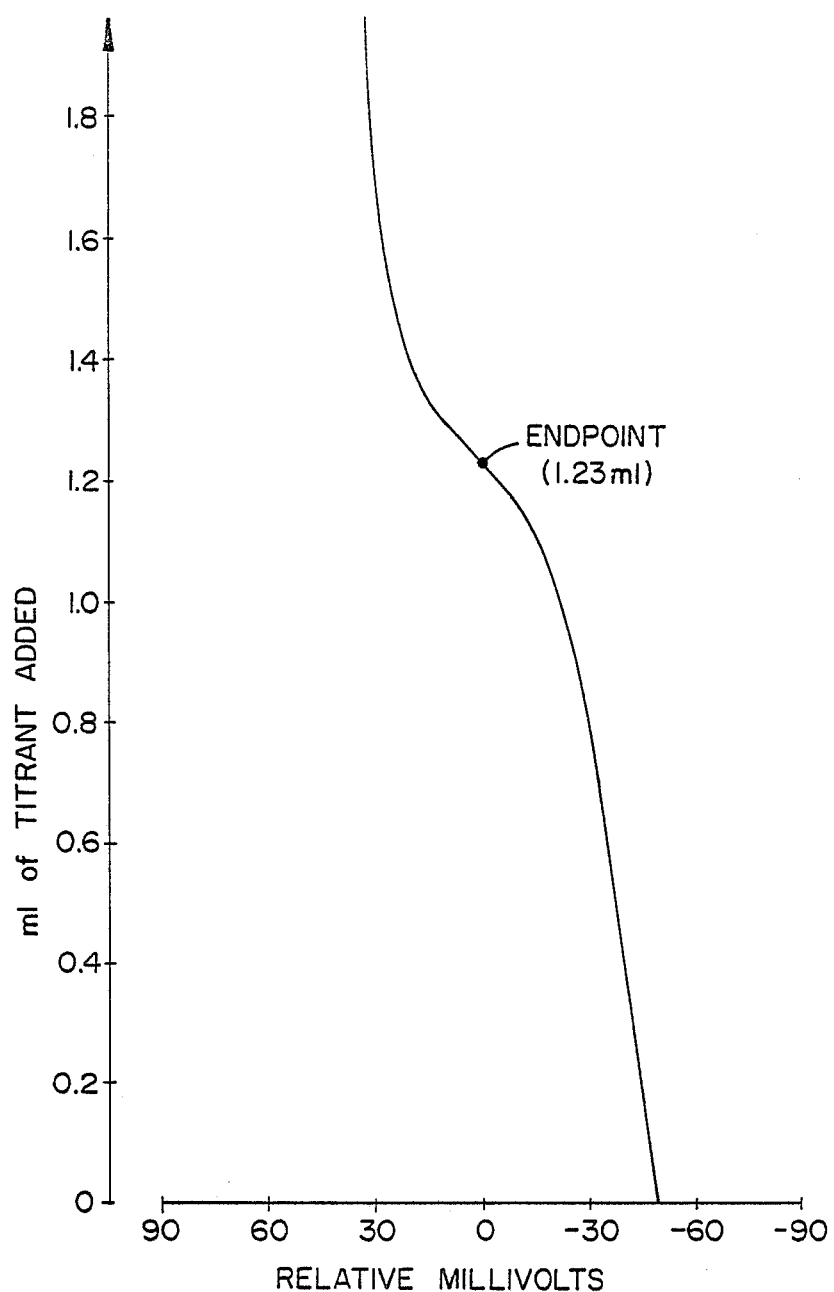
FIG._3.

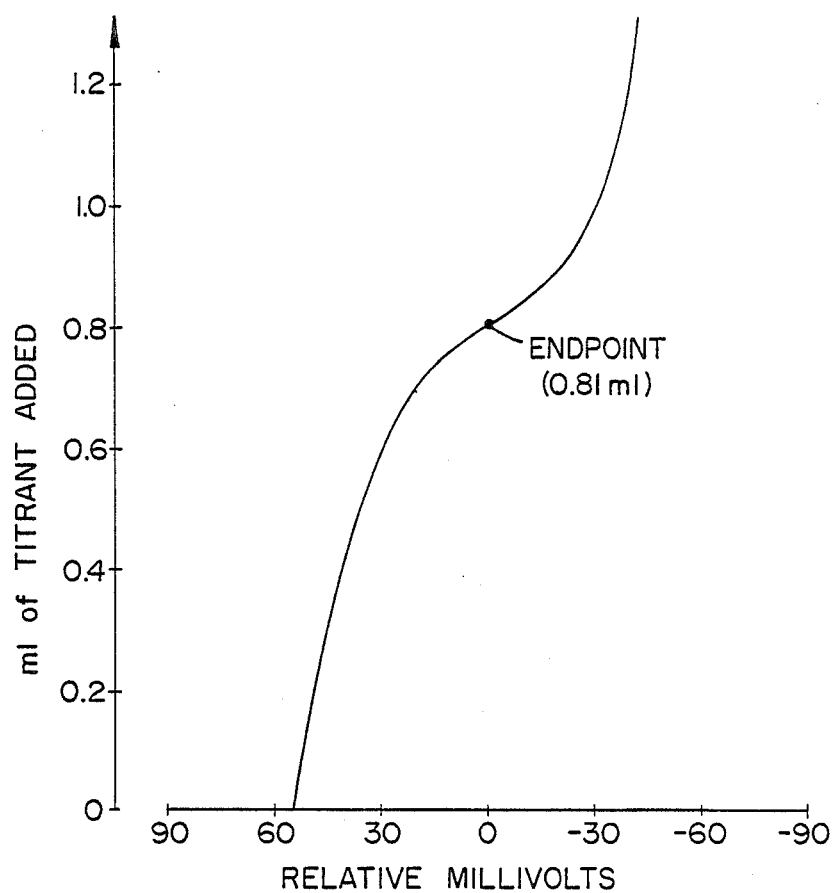
FIG._4.

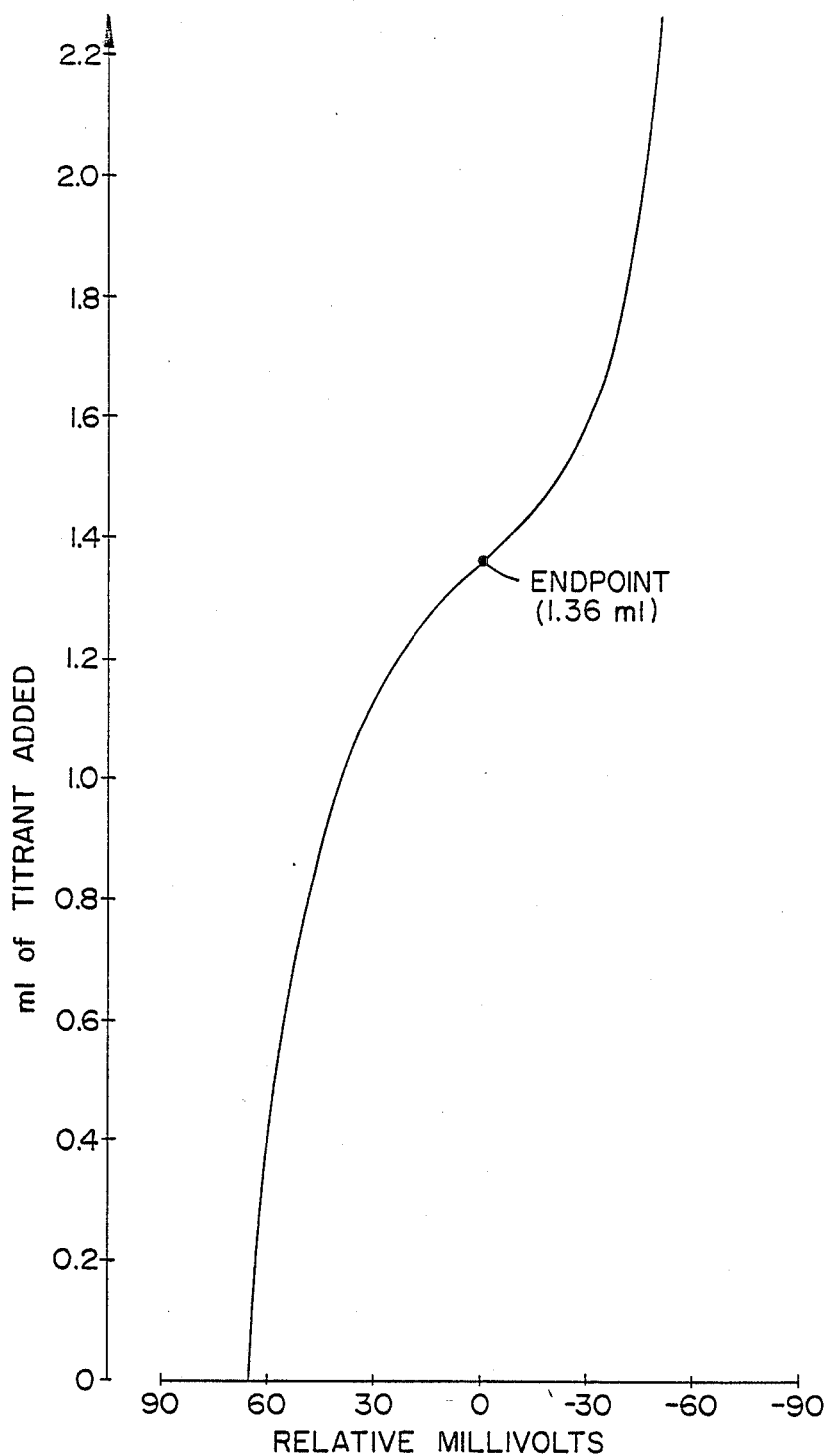
FIG._5.

SURFACTANT SENSING ELECTRODE FOR POTENTIOMETRIC TITRATIONS

BACKGROUND OF THE INVENTION

1. Field of the Invention

The present invention generally relates to sensing electrodes for titrations and, more particularly, to sensing electrodes for detecting the end points of potentiometric titrations of surfactants in solution.

2. State of the Art

In numerous instances, it is desirable to detect the concentration of surfactants in aqueous solutions. For example, to maintain product quality during production of commercial detergents and to assess product stability over time, it is necessary to test for the concentration of surfactants in solutions. Similar quantitation tests are required for the raw materials from which commercial detergents are compounded. Also during the formulation of new surfactant compounds and the development of new applications for surfactants, it is normally required to analytically test surfactant concentrations.

A surfactant can be broadly defined as an organic compound that encompasses two dissimilar structural groups, such as a water-soluble group and a water-insoluble group. Included within this definition are soaps and hydrotropes. The principal uses of surfactant compounds are in household detergent products. The critical characteristic of a surfactant is its surface activity including wetting and micellar solubilization. Surface activity of a surfactant molecule is determined by the composition, solubility properties, location and relative sizes of the dissimilar structural groups that make up the molecule. Various pairs of names have been used to designate the dissimilar groups: hydrophobic-hydrophilic, lipophobic-lipophilic, and oleophobic-oleophilic. Also, the terms polar and non-polar are often used to designate molecular surfactant groups that are soluble or insoluble, respectively, in water. The molecular weight of surfactants of commercial interest ranges from the low hundreds of grams per mole to a high of many thousands of grams per mole in the case of some hydrophilic polymers.

The hydrophilic or "solubilizing" groups in surfactants can be classified into four categories: anionic, cationic, amphoteric and nonionic. In anionic surfactants, the hydrophilic groups are negatively charged in aqueous solutions or dispersions. Anionic solubilizing groups include, for example, carboxylates, sulfonates, sulfates, and phosphates.

In cationic surfactants, hydrophilic groups bear a positive charge in aqueous solutions. Cationics are normally solubilized by amino groups, or quaternary nitrogens. To increase water solubility of cationic surfactants, additional amino groups can be introduced or an amino group can be quaternized with a low molecular weight alkyl group.

Amphoteric surfactants are those containing both an acidic and basic moiety in their structure. These may be any of the anionic or cationic groups, and a single amphoteric molecule may contain several ionic functions. Oxygens may also be present, as in nonionics, to strengthen the hydrophilic tendency of amphoteric molecules.

A nonionic surfactant, as the name implies, has essentially no charge when dissolved or dispersed in an aqueous medium. The hydrophilic tendency in nonionic molecules is due primarily to oxygen present in the form of alkoxy groups which interact with water molecules.

Chemical analysis of surfactants in aqueous solutions is of commercial importance and, specifically, it is often of commercial interest to determine the concentration, usually expressed in terms of moles per liter, of surfactant molecules, containing ten or more carbon atoms. The standard assay of anionic and cationic-active detergents in aqueous solutions is the two-phase Epton titration. This manual procedure is described by V. Reid, et al. in "Determination of Anionic-Active Detergents by Two-Phase Titration", Commission International d' Analyses, Milan, 1966. To determine stoichiometric endpoints in such titrations, three types of colorimetric indicators are commonly used: bromocresol green, methylene blue, and dimidium bromide-disulphine blue (DMB-DSB). Titrations with the mixed indicator DMB-DSB are described in "A Systematic Scheme of Semi-micro Qualitative Analysis for Anionic Surface-Active Agents," Holness, et al., Analyst, 1957, Vol. 82 pp 166-176. A typical stock solution of DMB-DSB is $2.63 \times 10^{-3}$ molar in DMB and $4.42 \times 10^{-4}$ molar in DSB and can be commercially obtained from British Drug House, Ltd., in Poole, England.

In a standard two-phase Epton titration, titrant is added to a surfactant solution until a color change in the indicator identifies the stoichiometric endpoint. It may be noted that DMB-DSB, changes color in response to either cationic or anionic surfactants. An advantage of two-phase titrations is that samples of both raw material surfactants and commercial detergent formulations can be titrated without substantial interference from other components in the samples; specifically, surfactant molecules containing ten or more carbon atoms can be titrated by two-phase titrations without substantially titrating lower molecular-weight substances or inorganic ions that are in the same sample solution. A drawback of two-phase titrations is that the time required for a typical analysis is about thirty minutes per sample. Also, because the non-aqueous phase in standard two-phase titrations is chloroform, analysts are exposed to a potential hepatotoxin when performing the assays. Further, the results of two-phase titrations with colorimetric indicators are subjective because color changes must be judged visually.

In the case of assays of anionic and cationic surfactant molecules containing more than ten carbon atoms, standard two-phase titrations are based upon the ion pairing of the surfactant molecule with a titrant of the opposite charge. For example, as measured quantities of cationic titrant are added to an aqueous surfactant solution of known volume, the cationic titrant displaces the cationic dye indicator causing a color change at the end point of the titration.

In the case of nonionic surfactants, common two-phase Epton titrations are not possible. An alternative titration technique requires the reagent 1,2-dichloroethane, which is a health hazard. As another alternative, quantitative analyses of nonionic surfactants are performed on high pressure liquid chromatography (HPLC) instruments, which also require relatively extensive sample preparation and hazardous solvents.

In view of the shortcomings of two-phase titrations of surfactants, workers in the art have attempted to devise potentiometric methods to perform the assays. In general, potentiometry requires assembling an electrochemical cell that has an indicator electrode sensitive to one of the ions to be studied and a reference electrode of fixed potential. The basic reference electrode is the standard hydrogen electrode; however, calibrated secondary reference electrodes, such as silver-silver chloride or mercury-calomel electrodes, are used in practice. In a potentiometric cell of typical design, the indicator electrode is surrounded by a solution of unknown ion concentration to which the electrode is sensitive, and the reference electrode is surrounded by a reference solution of known concentration. The electromotive force (e.m.f.) between the indicator electrode and the reference electrode of a potentiometric cell is related to ion activity which, in turn, is related to the concentration of ions in solution. More particularly, the e.m.f. across an ideal potentiometric cell (i.e., one that obeys the Nernst equation) is proportional to the logarithm of the activity of the ions in the solution to which the indicating electrode is sensitive.

In potentiometric cells for detecting concentrations of surfactant molecules, it is known to use ion-selective membrane electrodes that control ion migration between the reference solution and the test solution to be assayed. The membranes may be formed, for example, from an ion-selective glass material, an ion-selective polymeric material, or an ion-selective water-immiscible liquid. A liquid membrane electrode, for example, is described by Goina, et al. in "Potentiometric Titration of Sodium Cetyl Sulfate (NaCS) Using Liquid-Membrane Selective Ion Electrodes," Sosit la redactie, 16 April 1982. According to this reference, a suitable liquid membrane contains the solvent o-dichlorobenzene, an anionic surfactant, and one of the following dyes: crystal violet, malachite green, and methyl violet. Ion-selective polymeric membranes are also described in U.S. Pat. Nos. 3,562,129; 3,691,047; and 3,753,887. Such membranes are generally composed of a polymeric matrix in which is dispersed or dissolved a suitable cation-exchange material for a membrane that is to be sensitive to cations, or an anion exchange material for a membrane that is to be sensitive to anions.

In the case of potentiometric titrations, a titrant is added to a sample solution in an electrochemical cell to combine with ions in the solution. When the titrant is properly chosen, changes in the conductivity of the cell will be relatively abrupt at the end point of the titration. By electrometrically monitoring the e.m.f. of the cell during the titration, an inflection point on the titration curve can be identified which generally indicates the end point. In direct potentiometry, the e.m.f. between the indicator and reference electrodes is measured during titration by a suitable electrometric device.

With potentiometric titrations, automation becomes possible and analysis time can be substantially reduced. Also, potentiometric titrations minimize subjectivity in measurement because identification of colored endpoints is not necessary. However, a shortcoming of conventional potentiometric titrations is that indicating electrodes are normally responsive only to closely related homologues of the ion-exchange material bound in the membrane of the electrode. Furthermore, conventional indicating electrodes are responsive to only cationic or anionic surfactants, not both. Thus, indicating electrodes for potentiometric titrations normally must be carefully matched with the type of surfactant to be titrated and must be replaced when different types of surfactant are titrated.

A typical potentiometric cell is generally shown in U.S. Pat. No. 4,597,848. According to that patent, the indicating electrode is of the barrel-type and comprises a hollow body having a bottom closed by an ion-exchange membrane. The ion exchange membrane is formed of a solid polymer membrane of an anion-exchanger or a cation-exchanger, or may be amphoteric. A stable electrode, such as a calomel electrode, and the indicating electrode are immersed in an aqueous sample solution whose ion concentration is to be measured. Migration of ions between the sample solution and the solution within the indicating electrode is controlled by the ion-exchange membrane. The patent states that the indicating electrode with particular ion-exchange membranes is suitable to determine the activity of chloride ions in biological solutions. Another potentiometric cell using a barrel-type indicating electrode sensitive to amines is described in "PVC-Surfactant-Selective Electrode Responsive to Primary Amines," *Colloids and Surfaces,* 15 (1985) 277–283.

Ion-selective polymeric membranes are also discussed in "Film Ionselective Alkylsulfate Electrodes Based On Quaternary Ammonium Salts," A. Gulevich, et al., *Journal of Analytical Chemistry,* Vol. XL (1985), No. 9. The article describes a membrane electrode having a polyvinyl chloride (PVC) casing with adhesive electrode-active film consisting of PVC, dibutyl phthalate and alkylsulfate salts of trinonyl octadecyl ammonia as electro-active substances. According to the article, the electrode is reversible with respect to surfactants that include alkylsulfate anions.

For potentionmetric titrations of nonionic surfactants, ion-selective polymeric membranes are described in "Barium-Polyethoxylate Complexes and Potentiometric Sensors and Their Application to the Determination of Non-ionic Surfactants," D. Jones et al, Analyst, September, 1981, v. 106, pp. 974–984, and in USSR Author's Certificate No. 1,078,325A to V. Ivanov, et al. According to the latter publication, a membrane for a barrel-type electrode is formed of a matrix containing a salt of an anion and cationactive surfactant or nonionic surfactants complex with tetraphenylborate and barium cations. To make the electrode sensitive, a mixture of nonionic and cationic surfactants was used. Preparation and application of nonionic surfactant-selective electrodes is also described in an article by Qian Xixing, et al. appearing in *Fenxi Huaxue,* Vol. 13, No. 5 (1985), pp. 383–385.

An electrode selective only to organic cations is described in Japanese Patent Application No. 58-201240 disclosed 25 May 1985. According to that patent, the electrode is made from hydrophobic esterified or etherified dextrins dissolved in a polymer such as PVC containing a plasticizer such as dioctyl phthalate, dioctyl adipate, and tricresyl phosphate. The patent states that such electrodes are responsive to organic cations and some quaternary ammonium salts. The disclosed membrane material is said to be useful for both barrel-type electrodes and "coated-wire" electrodes.

In a coated-wire electrode, an ion-selective polymeric membrane is formed as an outer layer, or coating, on a conductive substrate such as a metallic wire. Such electrodes are discussed in "Surfactant-Sensitive Polymeric Membrane Electrodes," S. F. Cutler, et al., *Journal Electroanalytical Chemistry,* 1977, pp. 145–161, which describes the testing of a coated-wire electrode consisting of a platinum wire coated only with a thin film of plasticized PVC. According to the article, when the PVC did not contain any identifiable ion-exchange compound, the potentials of the coated-wire electrode responded to increasing concentrations of either cationic or anionic surfactants, but were irreproducible. The article reported that reproducible potentials were not obtained by incorporating an ion-exchange complex into the polymeric coating but were achieved when a dissolved plasticizing complex of a cationic and an anionic surfactant was incorporated into a PVC or polyvinyl bromide (PVB) matrix membrane. Specifically, the article reports that coated-wire electrodes providing reproducible potential measurements were made with PVC and PVB membranes plasticized with 40-60% tricresyl phosphate (TCP) or a pentaerythritol ester. It was further reported, however, that such electrodes became unstable or insensitive with prolonged usage (e.g., when immersed in concentrated surfactant solutions for periods exceeding six hours). The loss of stability was ascribed to solubilization of the ion-exchange complex. According to the article, solubilization was prevented by modifying the electrodes to have fixed charges chemically bound to the polymers and, specifically, by modifying the plasticized polymer membranes to contain cetyl trimethylammonium dodecyl sulphate. Such electrodes, referred to as chemically-modified polymer membrane electrodes, were said to react to either anionic or cationic surfactants according to the particular modifications made to the polymer.

Subsequent to the Cutler, et al. article, supra, it was reported in "Determination of Anionic-active Matter in Detergents by Potentiometric Titration," G. C. Dilley, Analyst, July, 1980, Vol. 105, pp. 713-719, that coated-wire electrodes as described by Cutler, et al. could be used to potentiometrically titrate a number of different anionic surfactants and that the electrodes provided potentiometric curves for which the titration endpoints could be reliably found. As indicated by its title, the article discussed efforts to adopt potentiometric titrations to detergents. Specifically, the article describes use of an ion-selective membrane in conjunction with a barrel-type electrode to potentiometrically indicate the endpoints of titrations of anionic-active matter in simple detergent solutions. For such usage, a suitable membrane was reported as containing only high relative mass PVC (40%) and tricresyl phosphate (60%) conditioned with a solution of sodium lauryl sulphate (SLS).

Coated-wire electrodes are also reported in Czechoslovakian patent No. 225,222 published December, 1984. According to an example provided in the patent, an ion-selective membrane was coated onto a conductive wire by repeatedly dipping the wire into a solution of PVC (85 mg), di-n-octyl phthalate (0.2 ml) and Reinecke acridine orange (0.5 mg) in the solvent tetrahydrofuran (THF). After each dipping, the solvent was evaporated until the conductive wire was covered with a membrane of predetermined thickness.

General operation of ion-selective coated-wire electrodes, as well as their application to various analytical problems involving organic species that are anionic or cationic, are discussed by L. Cunningham and H. Freiser in *Analytica Chimica Acta*, 180 (1986) 271-279. The authors particularly describe coated-wire electrodes for sensing high-molecular weight protonated amines in the physiologic pH range. According to the article, a coated-wire electrode was made by dipping the exposed end of an insulated wire into a solution containing an amine, 5% PVC in the solvent tetrahydrofuran (THF), 0.5% in dinonylnaphthalene sulfonic acid (DNNS), a lipophilic anionic extract, and 4.5% in plasticizer, usually dioctylphthalate. The coated-wire electrodes were said to be ready for use following conditioning in a $10^{-4}$ to $10^{-3}$M solution of the analyte.

In U.S. Pat. No. 4,399,002 to Freiser, et al., a coated-wire electrode is described that is sensitive to large organic cation species in aqueous test solutions. Specifically, the patent states that the membrane for the coated-wire electrode is composed of a polymeric matrix in which is dispersed or dissolved a cation exchange material whose counter-anion is said to be a high molecular weight alkyl or alkaryl sulfonate or sulphate of the formula $R(O)_nSO_3$ wherein n is 0 or 1, R is, for example, an alkyl group having at least 13 carbon atoms. According to the patent, such a membrane will generally include cation exchange material in amounts ranging from about 1% to about 25% by weight, and a plasticizer compatible with both the polymer and the cation exchange material in amounts ranging from about 10% to about 50% by weight of the membrane.

Further according to the patent, a suitable membrane may be prepared from a homogeneous solution of the cation exchange material, the polymer, and the optional plasticizer in an organic solvent such as an alcohol, a ketone, an ester, or a cyclic ether such as THF.

OBJECTS AND SUMMARY OF THE INVENTION

A primary object of the present invention is to provide a sensing electrode for potentiometric titrations which is sensitive to surfactant molecules that are charged, or capable of being charged, in aqueous solutions.

More particularly, an object of the present invention is to provide a sensing electrode such that, without changing its composition, the same electrode can be used for potentiometric titrations of anionic, cationic, and amphoteric surfactants as well as alkoxylated nonionic surfactants that have more than ten carbon atoms and that form complexes when titrated.

In accordance with the preceding, the present invention provides a coated-wire membrane electrode for potentiometric titrations of surfactants in an aqueous medium. The coated-wire electrode generally comprises an electrically conductive core member and a semipermeable membrane coated onto the core member. In the preferred embodiment, the semipermeable membrane consists of a matrix including a polymer, a plasticizer and an ion-exchange material consisting essentially of dimidium bromide-disulphine blue.

Further, the present invention provides a process for fabricating an indicating electrode to potentiometrically titrate surfactants in aqueous systems. Generally speaking, the process comprises the steps of: forming a core member of an electrically-conductive metal; preparing a liquid solution containing a solvent, a polymer matrix material, a plasticizing agent, and dimidium bromide-disulphine blue; and coating the core member with the liquid solution and then drying the coating to form a semipermeable ion-exchange membrane electrode.

An important advantage of the present invention is that it provides a potentiometric titration system that is capable of decreasing the time required for analysis of surfactant materials as compared to standard manual titration methods, while eliminating exposure of analysts to the organic solvents.

Additional objects and advantages of the present invention can be ascertained by reference to the following description and attached drawings which illustrate the preferred embodiment.

BRIEF DESCRIPTION OF THE DRAWINGS

FIG. 1 is a generally schematic diagram of a potentiometric titration cell employing an indicating electrode according to the present invention;

FIG. 2 is a detail view, partially cutaway for purposes of illustration, of an indicating electrode for use in the cell of FIG. 1; and FIGS. 3 through 5 are plots of potentiometric titrations of anionic, cationic and nonionic surfactants, respectively, employing the cell of FIG. 1.

DETAILED DESCRIPTION OF THE PREFERRED EMBODIMENT

FIG. 1 shows a potentiometric titration cell employing a sensing electrode 11 for detecting anionic, cationic, nonionic and amphoteric surfactants in aqueous samples. In the cell in FIG. 1, both sensing electrode 11 and a standard reference electrode 14, such as a calomel or silver-silver chloride electrode, are mounted in a container 13 that contains a sample surfactant solution 15 to be titrated. The non-immersed ends of electrodes 11 and 14 are electrically connected through a conventional electrometric device 27 that indicates the voltage between the electrodes. Generally speaking, the apparatus shown in FIG. 1 is conventional but for the construction of indicating electrode 11.

As shown in FIG. 2, sensing electrode 11 is generally a coated-wire electrode and includes an electrically conductive core member 31 having a portion coated with a semipermeable membrane 35 formulated in the manner described in the following. In practice, core member 31 is comprised of wire made of copper but silver, carbon, gold, aluminum, platinum and other conductive materials can be used. The body of conductive core 31, except for the immersed end, is sheathed by electrical insulation material 37. The non-sheathed portion of conductive core 31 is completely coated with semipermeable membrane 35.

Generally speaking, the base material for semipermeable membrane 35 is a polymer matrix. The polymer is preferably polyvinyl chloride (PVC), but other non-polar, relatively water-insoluble polymeric materials can be used. Specific examples of alternative polymeric materials include polyvinyl butyryl, polyvinyl bromide, copolymers of polyvinyl alcohol with an appropriate comonomer such that the copolymer is insoluble, and mixtures thereof.

To form membrane 35, the polymer base material is treated with a plasticizer and a suitable quantity of DMB-DSB which, ultimately, becomes bound in the semipermeable matrix. When the polymer is PVC, the preferred plasticizer is tritolyl phosphate but other polar plasticizers can be used including phthalic acid derivatives, such as dioctyl phthalate, 2-nitrophenyl alkyl ether, sebacic acid derivatives such as di-n-alkyl sebacate, and oxalic acid derivatives such as di-n-alkyl oxalate, and mixtures thereof. Although selection of a plasticizer will depend upon the polymeric material used in the membrane, the plasticizer generally should be a material that lowers the glass transition temperature, Tg, of the polymeric membrane material to a temperature below normal operating temperature (e.g., about 60°-90° F.) when added in a plasticizing-effective amount. The ratio of the quantity of polymer to the quantity of plasticizer (by weight) ranges at least from about 10:1 to about 1:10 and, preferably, is within the range of about 3:2 to 2:3.

Generalized structures of DMB and DSB molecules are shown below.

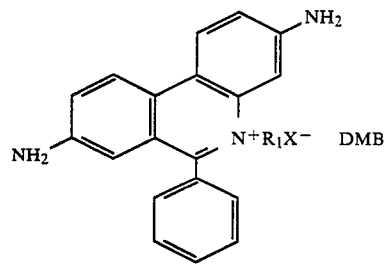

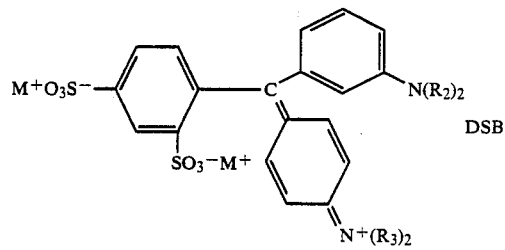

In the structural diagram, $M^+$ is any alkali metal or alkaline-earth metal, preferably sodium. $X^-$ is any halide or small anion such as methylsulfate or tetrafluoroborate, and preferably $X^-$ is bromide or iodide. $R_1$ is hydrogen, methyl, ethyl, propyl or butyl, and preferably is methyl. $R_2$ and $R_3$ are the same or different and may be hydrogen, methyl, ethyl, propyl isopropyl, butyl, and isobutyl. Preferably $R_2$ and $R_3$ are both ethyl. In the following, the abbreviation DMB-DSB will be used to designate the two molecular structures illustrated above; thus, the abbreviation should be understood to encompass dimidium bromide and disulphine blue molecules as well as the homologues. Also in the following, the term dimidium bromide-disulphine blue will be used to specifically refer to DMB-DSB wherein $R_1$ is methyl, $R_2$ and $R_3$ are ethyl, $X^-$ is bromide and $M^+$ is sodium.

The process for forming sensing electrode 11 includes providing a liquid mixture of polymer material, plasticizer, DMB-DSB and a suitable solvent such as THF and cyclohexane. Conductive core 31 is coated with the liquid mixture which, upon drying, forms a semipermeable ion-selective membrane encapsulating the core. A specific example of the formulation of a suitable semipermeable matrix material will now be provided. In comparison to other formulations, the formulation described below produces superior membranes as evaluated by electrode-to-electrode consistency, by the size of inflections produced during potentiometric titrations, and by the fact that the same sensing electrode can be used for potentiometric titrations of cationic, anionic, nonionic and amphoteric surfactants.

Example of Formulation of Coating Solution:

According to this example, the coating solution was prepared using 0.70 ml of tritolyl phosphate plasticizer (TTP) stirred into 10 ml of the solvent THF. Then, 0.54 g of PVC was slowly added and stirred until the solution became clear. At this point, the solution can be described as being about 40% PVC/60% plasticizer by weight, based upon the assumption that the density of the plasticizer is about one gram per milliliter and disregarding the weight of the solvent.

Next, 10 grams of PVC/plasticizer/THF solution was mixed with 2 grams of commercially-prepared dimidium bromide-disulphine blue solution having a concentration of about $2.6 \times 10^{-3}$M DMB and about $4.4 \times 10^{-4}$M DSB without further purification. The dimidium blue-disulphine blue was obtained from British Drug House, Ltd. At this point in the example, the solution can be described as about 40% PVC/60% plasticizer/20% DMB-DSB by weight in the stock solution of dimidium bromide-disulphine blue. The rationale for this description is that 10 grams of the solution which was 40% PVC/60% plasticizer (including solvent) were mixed with 2 grams of the dimidium bromide-disulphine blue stock solution. It should be noted that the sum of the weight percents of PVC and the plasticizer total to 100%, disregarding the weight of the solvent. The ratio of the quantity of dimidium bromide-disulphine blue stock solution to the sum of the weights of the polymer and plasticizer plus solvent can range from at least about 1:20 to about 1:1 by weight and, preferably, is within the range of about 1:10 to about 4:10, with the optimum being about 2:10. In terms of dry weight percent, the described membrane is about 0.138% dimidium bromide, 0.043% disulphine blue, 44.3% TTP, and 55.51% PVC.

Further according to this example, after addition of the dimidium bromide-disulphine blue solution, a gelled fraction formed. After prolonged shaking, the gelled and liquid fractions were filtered through a coarse crucible; the liquid separated and a purple residue was left in the crucible. The residue was transferred to another vial that contained two milliliters of the solvent THF and was stirred until solubilized. The resulting blue-purple viscous solution was used to coat conductive core 31 as discussed above. In practice, the dry weight percent of dimidium bromide in the membrane can range from about 0.01 percent to about 15% and, preferably, from about 0.05% to about 5%. Also in practice, the dry weight percent of disulphine blue can range from about 0.004% to about 5% and, preferably, from about 0.01% to about 2%.

Example of Formation of a Sensing Electrode:

A sensing electrode was made from an 8-gauge copper wire about six inches in length. The wire was insulated with electrical tape except for the bottom one-half inch. The exposed end of the wire was polished until shiny and then rinsed with acetone. Then the exposed end of the wire was dipped three times into the above-described coating solution and was allowed to dry after each dip. After evaporation of the solvent, the wire was observed to be coated with a thin membrane having a shiny blue-purple color. Preferably, the membrane is about 100 microns thick; however, functional membranes can be constructed with thicknesses ranging from about twenty to about one thousand microns.

In the preferred embodiment, the composition of membrane 35 of sensing electrode 11 of FIG. 2 is about 20% in the stock solution of dimidium bromide-disulphine blue prior to filtration and drying. The performance of a membrane of this composition versus other compositions can be observed from the information reported in Tables I through IV below. As listed in Table I, data was obtained by potentiometric titrations of raw material anionic surfactants, raw material quaternary ammonium salt surfactants, and raw material amphoteric surfactants. In the table, the name Adogen designates Adogen 471 trimethyl tallow ammonium chloride as provided by the Sherex Chemical Company; Alfonic designates Alfonic 1412-S sulfated ethoxylated alcohol, sodium salt as provided by Conoco Chemical Company; LAS designates LAS sodium alkyl aryl sulfonate identified under the trademark Calsoft F-90 by Pilot Chemical Company; SAS designates secondary alkane sulfonate, sodium salt identified under the trademark Hostapur SAS 60 by American Hoechst Corporation; and BTC designates benzalkonium chloride identified under the trademark Onyx BTC 50 by Onyx Chemical Company. The amine oxide is a N,N-dimethyl dodecyl amine oxide, available from Aldrich Chemical Company. Neodol designates neodol 23-6.5, a product of the Shell Chemical Company.

TABLE I

| Surfactant | Tested Surfactants Wt. %[1] | Molecular Wt. |
|---|---|---|
| Adogen | 50.5 | 339 |
| Alfonic | 58.0 | 435 |
| LAS | 86.8 | 342 |
| SAS | 27.2 | 328 |
| BTC | 44.9 | 361 |
| Amine oxide | 95.6 | 229 |

[1]Weight percent calculated from two-phase titration data.

Table II shows results of potentiometric titrations using the electrode 11 of FIG. 1 having a membrane composition of 40% PVC/60% Plasticizer with various levels of dimidium bromide-disulphine blue. In the table, the abbreviation meq/g designates milliequivalents of titer per gram of sample. Table III shows the results obtained for potentiometric titrations using coated-wire electrode 11 of FIG. 1 having a membrane composition of 50% PVC/50% plasticizer and various selected levels of dimidium bromide-disulphine blue. Table IV shows potentiometric titration results of tests using coated-wire electrodes having a membrane composition of 60% PVC/40% plasticizer and various levels of dimidium bromide-disulphine blue. The potentiometric titration results for each membrane composition were compared to results obtained by two-phase titrations.

TABLE II

| | | 40% PVC/60% Plasticizer | | | | |
|---|---|---|---|---|---|---|
| | | meq/g | | Weight % | | Relative % Deviation |
| Surfactant | Membrane | two-phase | Potentiometry | two-phase | Potentiometry | Potentiometry vs. two-phase[1] |
| Adogen | 10% DMB-DSB | 1.50 | 1.48 | 50.5 | 50.2 | −1.33 |
| Adogen | 20% DMB-DSB | 1.50 | 1.50 | 50.5 | 50.4 | 0 |
| Adogen | 30% DMB-DSB | 1.50 | 1.51 | 50.5 | 50.8 | 0.67 |
| Alfonic | 10% DMB-DSB | 1.33 | 1.26 | 58.0 | 55.0 | −5.26 |
| Alfonic | 20% DMB-DSB | 1.33 | 1.34 | 58.0 | 58.4 | 0.75 |
| Alfonic | 30% DMB-DSB | 1.33 | 1.30 | 58.0 | 56.8 | −2.26 |
| LAS | 10% DMB-DSB | 2.54 | 2.43 | 86.8 | 83.1 | −4.33 |
| LAS | 20% DMB-DSB | 2.54 | 2.50 | 86.8 | 85.6 | −1.57 |

TABLE II-continued

40% PVC/60% Plasticizer

| Surfactant | Membrane | meq/g two-phase | meq/g Potentiometry | Weight % two-phase | Weight % Potentiometry | Relative % Deviation Potentiometry vs. two-phase[1] |
|---|---|---|---|---|---|---|
| LAS | 30% DMB-DSB | 2.54 | 2.52 | 86.8 | 86.3 | −0.79 |
| BTC | 20% DMB-DSB | 1.25 | 1.26 | 44.9 | 45.6 | 0.80 |
| BTC | 30% DMB-DSB | 1.25 | 1.20 | 44.9 | 43.3 | −4.00 |
| SAS | 20% DMB-DSB | 0.83 | 0.82 | 27.2 | 26.9 | −1.20 |
| SAS | 30% DMB-DSB | 0.83 | 0.81 | 27.2 | 26.7 | −2.41 |

[1] Relative percent deviation is based upon meq/g values.

TABLE III

50% PVC/50% Plasticizer

| Surfactant | Membrane | meq/g two-phase | meq/g Potentiometry | Weight % two-phase | Weight % Potentiometry | Relative % Deviation Potentiometry vs. two-phase[2] |
|---|---|---|---|---|---|---|
| Adogen | 10% DMB-DSB | 1.50 | 1.45 | 50.5 | 49.2 | −3.33 |
| Adogen | 20% DMB-DSB | 1.50 | 1.48 | 50.5 | 49.6 | −1.33 |
| Adogen | 30% DMB-DSB | 1.50 | 1.48 | 50.5 | 49.6 | −1.33 |
| Adogen | 40% DMB-DSB | 1.50 | 1.47 | 50.5 | 49.2 | −2.00 |
| Alfonic | 10% DMB-DSB | 1.33 | 1.26 | 58.0 | 55.0 | −5.26 |
| Alfonic | 20% DMB-DSB | 1.33 | 1.29 | 58.0 | 56.4 | −3.01 |
| Alfonic | 30% DMB-DSB | 1.33 | [1] | 58.0 | [1] | [1] |
| Alfonic | 40% DMB-DSB | 1.33 | 1.29 | 58.0 | 56.4 | −3.01 |
| LAS | 10% DMB-DSB | 2.54 | 2.42 | 86.8 | 82.8 | −4.72 |
| LAS | 20% DMB-DSB | 2.54 | 2.54 | 86.8 | 86.6 | 0 |
| LAS | 30% DMB-DSB | 2.54 | 2.50 | 86.8 | 85.6 | −1.57 |
| LAS | 40% DMB-DSB | 2.54 | 2.50 | 86.8 | 85.6 | −1.57 |
| BTC | 20% DMB-DSB | 1.25 | 1.21 | 44.9 | 43.7 | −3.20 |
| BTC | 30% DMB-DSB | 1.25 | 1.19 | 44.9 | 43.2 | −4.80 |
| BTC | 40% DMB-DSB | 1.25 | 1.17 | 44.9 | 42.2 | −6.40 |
| SAS | 20% DMB-DSB | 0.83 | 0.85 | 27.2 | 27.9 | 2.41 |
| SAS | 30% DMB-DSB | 0.83 | 0.86 | 27.2 | 28.1 | 3.61 |
| SAS | 40% DMB-DSB | 0.83 | 0.84 | 27.2 | 27.6 | 1.20 |

[1] No endpoint was obtained
[2] Using meq/g values

TABLE IV

60% PVC/40% Plasticizer

| Surfactant | Membrane | meq/g two-phase | meq/g Potentiometry | Weight % two-phase | Weight % Potentiometry | Relative % Deviation Potentiometry vs. two-phase |
|---|---|---|---|---|---|---|
| Adogen | 10% DMB-DSB | 1.50 | 1.46 | 50.5 | 49.49 | −2.67 |
| Alfonic | 10% DMB-DSB | 1.33 | [1] | 58.0 | [1] | [1] |
| LAS | 10% DMB-DSB | 2.54 | 2.45 | 86.8 | 83.8 | −3.54 |

[1] No endpoint was obtained
[2] Based upon meq/g values

The information in Table II reveals that the best results among the membrane materials were obtained for the 20% DMB-DSB membrane. As to the tested raw material surfactants, the data tabulated in Table II shows relative deviations for potentiometric titration versus two-phase titrations of −1.57% to 0.80% for the 20% DMB-DSB membrane. Also for 20% DMB-DSB membranes, data in Table III reveals relative percent deviations range from −3.2% to 2.4%. Upon comparison of the information displayed in Tables II-IV, it can be concluded that potentiometric titration results that correlated best with two-phase titrations were obtained for an electrode that was 40% PVC/60% plasticizer/20% DMB-DSB; such an electrode exhibited a relative percent deviation of about −1.57% to 0.8%.

The following provides an example of potentiometric titrations employed to generate information such as in Tables II to IV. The example also shows a comparison of results obtained by potentiometric titration using a coated-wire electrode versus results obtained from commercially-available titration machines.

Titration Example:

After fabrication, a coated-wire electrode (40% PVC/60% plasticizer/20% DMB-DSB) was immersed in sample aqueous solutions containing unknown concentrations of identified surfactants. A silver-silver chloride reference electrode was also immersed in each of the solutions. The surfactants chosen for titration are listed in Table V and included commercial detergents as well as raw material surfactants. For comparison purposes, titrations were also performed on a Radiometer A/S RTS 822 autotitrator and on a Fisher Computer Aided Titrometer (CAT) autotitrator. The titrants were Hyamine 1622[R] (HYM), a trademarked product of Rohm & Hass Company, and sodium lauryl sulphate (SLS). Both titrants were prepared with deionized water as solvent. The SLS titrant was assayed for purity by acid hydrolysis and the HYM titrant was standardized against it. After each titration, the coated-wire electrode was rinsed with deionized water to prevent precipitates from coating its membrane.

of raw materials and detergent formulations that contain surfactant molecules having ten or more carbon atoms without substantial interference from common

TABLE V

Comparisions of Two-Phase Titrations Using 40% PVC/60% Plasticizer/20% DMB-DSB Coated Wire Electrode

| | meq/g | | | Weight % | | | Relative % Deviation[1] | |
|---|---|---|---|---|---|---|---|---|
| | | | | | | | CAT vs. | Radiometer vs. |
| Sample | two-phase | CAT | Radiometer | two-phase | CAT | Radiometer | two-phase | two-phase |
| Adogen | 1.50 | 1.50 | 1.49 | 50.4 | 50.4 | 50.2 | 0.13 | −0.36 |
| Alfonic | 1.33 | 1.34 | 1.35 | 58.0 | 58.4 | 58.7 | 0.75 | 1.12 |
| LAS | 2.54 | 2.50 | 2.56 | 86.8 | 85.6 | 87.4 | −1.57 | 0.70 |
| SAS | 0.83 | 0.82 | 0.79 | 27.2 | 26.9 | 26.0 | −1.20 | −4.74 |
| BTC | 1.25 | 1.17 | 1.18 | 44.9 | 42.2 | 42.4 | −6.40 | −5.57 |
| Amine oxide | 4.17 | N/A | 4.21 | 95.6 | N/A | 96.6 | N/A | −1.07 |
| Oxydol | 0.623 | 0.645 | 0.690 | N/A | N/A | N/A | 3.53 | 10.8 |
| Surf | 0.480 | 0.508 | 0.522 | N/A | N/A | N/A | 5.83 | 8.75 |
| Dynamo | 0.179 | 0.192 | 0.207 | N/A | N/A | N/A | 7.26 | 15.6 |
| Era Plus | 0.233 | 0.277 | 0.255 | N/A | N/A | N/A | 18.9 | 9.44 |
| Gain | 0.426 | 0.434 | 0.395 | N/A | N/A | N/A | 1.88 | −7.28 |
| Tide | 0.534 | 0.547 | 0.524 | N/A | N/A | N/A | 2.43 | −1.87 |
| Cheer | 0.380 | N/A | 0.430 | N/A | N/A | N/A | N/A | 13.2 |

[1]Based upon meq/g.

For raw material surfactants and commercial detergents, Table V reveals good agreement between the majority of the two-phase and potentiometric titrations. In the case of raw material surfactants, the average deviation is −2.83% for comparisons with the CAT autotitrator and 2.23% for comparisons with the Radiometer autotitrator. For analysis on the CAT autotitrator, commercial detergents that fall within 10% relative deviation are Oxydol[R], Surf[R], Dynamo[R], Gain[R], and Tide[R]. For analysis on the Radiometer autotitrator, commercial detergents falling within the 10% relative deviation are Oxydol[R], Surf[R], Era Plus[R], Gain[R], and Tide[R].

FIGS. 3 through 5 show plots obtained from potentiometric titrations of anionic, cationic and nonionic surfactants, with electrode 11 of FIGS. 1 and 2. FIG. 3 shows the titration curve for 1 ml of 0.004M SLS titrated with 0.00328M Hyamine; the endpoint of this titration occurred when 1.23 ml of titrant was added. FIG. 4 shows the titration curve for 1 ml of 0.00328M Hyamine titrated with 0.004M SLS; the endpoint of the titration occurred when 0.81 ml of titrant was added. FIG. 5 shows the titration curve for 1 ml of 0.004M Neodol 23-6.5 titrated with sodium tetraphenyl borate; at the endpoint of the titration, 1.36 ml of the titrant had been added. It should be noted that the same coated-wire electrode was used in each titration.

Another advantage of a coated-wire electrode 1 of FIG. 1 is that it can be used for potentiometric titrations inorganic ions or smaller organic molecules. Such selectivity of the coated-wire electrodes was demonstrated as described in the following.

Example of Electrode Selectivity:

Laboratory samples of a simulated commercial detergent containing 8.2% phosphorus were made without surfactants. Then surfactants were added to the samples to achieve final surfactant concentrations ranging from approximately 8% to about 15% by weight. Prior to mixing with the simulated detergent, the surfactants were potentiometrically titrated to determine the "expected results" reported in Table VI. Then mixtures of the simulated detergent with the surfactants were potentiometrically titrated to provide the "observed" values reported in Table VI.

The potentiometric titrations listed in Table VI employed oppositely-charged titrants; for example, SLS and LAS were titrated with 0.004M Hyamine 1622[R]. The raw material amine oxide and detergent solutions of amine oxide were acidified to pH 1.7 with 1M HCl to protonate the amine oxide and then were titrated with either sodium tetraphenyl borate at 0.008M, or with SLS at 0.004M. The Neodol 23-6.5 was treated with an excess of BaCl$_2$ (0.2M) to form a cationic complex which was then titrated with sodium tetraphenyl borate.

TABLE VI

Surfactant Analysis in a detergent matrix using coated-wire electrode

| Analyte | Expected Result | Observed Result | Relative % Error |
|---|---|---|---|
| SLS | 3.32 meq/g | 3.44 ± 0.025 meq/g | 3.6% |
| | 3.36 meq/g | 3.39 ± 0.023 meq/g | 0.09% |
| LAS | 2.25 meq/g | 2.58 ± 0.04 meq/g | 0.98% |
| | 2.48 meq/g | 2.48 ± 0.076 meq/g | 0 |
| Neodol | 2.55 meq/g | 2.48 ± 0.045 meq/g | −2.7% |
| | 2.50 meq/g | 2.51 ± 0.08 meq/g | 0.40% |
| Amine Oxide | 5.35 meq/g | 5.31 ± 0.035 meq/g | 0.75% |
| Amine Oxide | 4.17 meq/g | 4.17 ± 0.045 meq/g | 0 |
| LAS + Neodol[1] | (2.57 meq/g | 2.56 ± 0.049 meq/g | −0.4% |
| | (1.26 meq/g | 1.26 ± 0.38 meq/g | 0% |

[1]Titration of LAS and Neodol done sequentially; the upper row shows results for LAS and the lower for Neodol.

The information in Table VI indicates no substantial interference from inorganic ions during potentiometric titrations of detergent matrices using the coated-wire electrode 11 of FIGS. 1 and 2. In other words, relative errors from such titrations were within acceptable ranges for analytical procedures. Additionally, Table VI indicates that nonionic surfactants that cannot be titrated by conventional two-phase titration methods using DMB-DSB as a colorimetric indicator can be successfully titrated by potentiometric methods using the coated-wire electrode 11 of FIGS. 1 and 2.

ated that potentiometric titrations employing the coated-wire electrode 11 of FIG. 1 are effective for determining the concentrations of such nonionic surfactants in aqueous solution. Furthermore, as compared to two-phase titrations and assay analyses with HPLC instruments, potentiometric titration of such nonionic surfactants is relatively fast and inexpensive; additional benefits are that sample preparation is minimal and that the titrations are performed in aqueous media.

TABLE VII

| Sample | Potentiometric titration of nonionic surfactants | | |
|---|---|---|---|
| | Expected Result | Observed Result | Relative % Error |
| Liquid peroxygen-containing laundry adjunct | 0.129 meq/g | 0.112 meq/g | (1) |
| Paste detergent with phosphates | 1.05 meq/g | 1.04 meq/g | (1) |
| Paste detergent without phosphates | 0.880 meq/g | 0.830 meq/g | (1) |
| Thickened laundry adjunct | 0.255 meq/g | 0.258 meq/g | 1.2% (2) |
| Granular detergent | 0.092 meq/g | 0.092 meq/g | 0 (2) |
| Granular detergent | 0.175 meq/g | 0.165 meq/g | −5.7% (2) |
| Granular detergent | 0.223 meq/g | 0.236 meq/g | 5.8% (2) |
| Granular detergent | 0.274 meq/g | 0.285 meq/g | 4.0% (2) |
| Granular detergent | 0.386 meq/g | 0.387 meq/g | −0.26% (2) |

(1) The expected result is the process target value, not on experimentally determined value; thus, relative error is inappropriate.
(2) The expected result is based upon known amounts of nonionic surfactant added directly to the detergent matrix.

To form mixed-surfactant systems to test the sensitivity of coated-wire electrode 11, LAS and Neodol 23-6.5 were added to sample solutions containing the simulated detergent. Then aqueous barium chloride (0.2M) was added to the sample solution to form a precipitate (i.e., the barium salt of LAS). As listed in Table VI, the expected result of titration of Neodol was 2.57 meq/g and the observed result was 2.56±0.049 meq/g. When LAS was titrated with Hyamine 1622R, the expected result was 1.26 meq/g and the observed result was 1.26±0.038 meq/g.

Another important application for the coated-wire electrode 11 of FIG. 1 is potentiometric titrations of nonionic surfactants that contain oxygen molecules in the form of alkoxy groups that form complexes with multivalent metal cations such as barium and calcium ions. Generally speaking, potentiometric titrations of such surfactants include a step whereby the surfactant is complexed with an ion, such as a multivalent metal ion, which places a net charge on the surfactant molecule. Amphoteric surfactant molecules can be similarly charged or maintained at a pH which renders them charged. A method for conducting such titrations is set forth in the following example.

Example of potentiometric titration of nonionic surfactants:

Samples of an alkoxylated nonionic surfactant were dissolved in water. Barium chloride (BaCl$_2$) was prepared in deionized water at a concentration of 0.2M, and added to the sample abundantly. The samples were then titrated potentiometrically with 0.008M sodium tetraphenylborate. For samples containing a mix of the nonionic substances of differing molecular weights, the total theoretical milliequivalents per gram (meq/g) was calculated from standard curves and the titration of the product was evaluated versus the target value.

Table VII displays results of potentiometric titrations of alkoxylated nonionic detergents, particularly ethoxylated nonionic detergents, according to the above-described technique. From Table VII, it can be appreci- It should be appreciated that potentiometric quantitation of surfactant samples using a coated-wire membrane electrode as described above can be automated by employing an autosampler in conjunction with a potentiometric titration instrument. In some cases, such potentiometric titrations may take as little as two minutes per sample, compared with thirty minutes per sample when using manual two-phase titration methods or chromatographic procedures.

In view of the preceding, it can be appreciated that the present invention provides a sensing electrode having a semipermeable membrane including a DMB-DSB ion-pair for potentiometric quantitation of alkoxylated nonionic surfactants as well as anionic, cationic and amphoteric surfactants. Stated somewhat differently, the same electrode can be used for potentiometric titrations of anionic, cationic and amphoteric surfactants as well as nonionic surfactants that form water-insoluble complexes when titrated. Moreover, the coated-wire electrode is selective in sensing surfactant molecules containing ten or more carbon atoms in mixtures containing relatively low-molecular-weight organic compounds or inorganic ions.

Although the present invention has been described with particular reference to preferred embodiments, such disclosure should not be interpreted as limiting. For example, although potentiometric titrations have been emphasized, sensing electrode 11 of FIG. 1 can be used for direct potentiometry under appropriate circumstances, and thus has application to on-line potentiometric monitoring of surfactant and detergent manufacturing systems. Also, although emphasis has been given to use of the DMB-DSB semipermeable membrane material on coated-wire electrodes, the material may be used in appropriate barrel-type electrodes. These and other alterations and modifications to the preferred embodiments will no doubt become apparent to those skilled in the art after having read the preceding disclosure. It is intended that the appended claims be interpreted as covering all alternative embodiments and equivalents as fall within the scope of the following claims.

What is claimed is:

1. A coated-wire electrode for potentiometrically titrating anionic, cationic, nonionic and amphoteric surfactants in an aqueous medium, comprising:
   an electrically-conductive core member;
   a semipermeable membrane which coats the core member, the membrane comprising a semipermeable matrix including a polymer, a plasticizer and an ion-exchange material consisting essentially of DMB-DSB in suitable proportions to be surfactant sensitive.

2. A coated-wire electrode according to claim 1 wherein the polymer is selected from the group consisting of polyvinyl chloride, polyvinyl butryl, polyvinyl bromide, insoluble copolymers of polyvinyl alcohol, and mixtures thereof.

3. A coated-wire electrode according to claim 1 wherein the plasticizer is a polar substance.

4. A coated-wire electrode according to claim 3 wherein the plasticizer is a material that lowers the glass transition temperature of the membrane to a temperature below about 60° F.

5. A coated-wire electrode according to claim 1 wherein the DMB-DSB is dimidium bromide-disulphine blue and its content in the membrane, in terms of dry-weight percent, ranges from about 0.014% to about 20%.

6. A coated-wire electrode according to claim 1 wherein the DMD-DSB is dimidium bromide-disulphine blue and its content in the membrane, in terms of dry-weight percent, ranges from about 0.06% to about 7%.

7. A coated-wire electrode according to claim 1 where in the plasticizer is a substance that lowers the glass transition temperature of the membrane to a temperature below about b 60° F.

8. A membrane for an electrode that is potentiometrically sensitive to anionic, cationic, nonionic, and amphoteric surfactants in an aqueous medium, comprising:
   a matrix including a polymer, a plasticizer and an ion-exchange material consisting essentially of dimidium bromide-disulphine blue in suitable proportions to be sensitive to surfactants.

9. A membrane according to claim 8 wherein the dimidium bromide-disulphine blue content in the membrane, in terms of dry-weight percent, ranges from about 0.06% to about 7%.

10. A sensing electrode for use in potentiometric titrations of surfactants in aqueous systems fabricated in steps comprising:
    (a) forming a core member of an electrically-conductive material;
    (b) preparing a liquid mixture by combining a stock solution of DMB-DSB- a solvent, a semipermeable matrix material, and a plasticizing agent; and
    (c) coating thecore member with the liquid mixture and drying the coating to form an ion-exchange membrane electrode.

11. A sensing electrode according to claim 10 wherein the DMB-DSB is dimidium bromide-disulphine blue and its content in the membrane, in terms of weight percent of stock solution of DMB-DSB compared to weight percent of the polymer, the plasticizer, and the solvent in the solution that forms the membrane ranges from about 1:20 to about 1:1.

12. A sensing electrode according to claim 10 wherein the DMB-DSB is dimidium bromide-disulphine blue and its content in the membrane, in terms of weight percent of stock solution of DMB-DSB compared to weight percent of the polymer, the plasticizer and the solvent in the solution that forms the membrane ranges from about 1:10 to about 4:10.

13. A sensing electrode according to claim 10 wherein the DMB-DSB is dimidium bromide-disulphine blue and its content in the membrane, in terms of weight percent of stock solution of DMB-DSB compared to weight percent of the polymer, the plasticizer, and the solvent in the solution that forms the membrane of about 2:10.

14. A sensing electrode according to claim 10 wherein the plasticizer is tritolyl phosphate, present in a plasticizing-effective amount.

15. A sensing electrode according to claim 10 wherein the DMB-DSB is dimidium bromide-disulphine blue present in suitable proportion to be surfactant sensitive.

16. A sensing electrode according to claim 10 wherein the semipermeable matrix material is selected from the group consisting of polyvinyl chloride, polyvinyl butryl, polyvinyl bromide, and insoluble copolymers of polyvinyl alcohol, and mixtures thereof.

17. A process for forming a sensing electrode to potentiometrically titrate surfactant molecules having ten or more carbon atoms in aqueous systems comprising the steps of:
    (a) preparing a liquid solution containing a solvent, a polymer, a plasticizing agent, and DMB-DSB;
    (b) stirring the liquid solution;
    (c) from the solution, separating a gelled fraction and a liquid fraction;
    (d) dissolving the gelled fraction in solvent; and
    (e) coating an electrically conductive core member with the dissolved gelled fraction and drying the coating to form an ion-exchange membrane.

18. A process according to claim 17 wherein the DMB-DSB content in the membrane, in terms of weight percent of a stock solution of DMB-DSB compared to weight percent of the polymer, the plasctizer and the solvent in the solution is about 2:10.

19. A process according to claim 17 wherein the DMB-DSB content in the membrane, in terms of weight percent of a stock solution of DMD-DSB compared to weight percent of the polymer, the polasticizer and the solvent in the solution, ranges from at least about 1:20 to about 1:1.

20. A process for potentiometrically titrating alkoxylated nonionic surfactants in aqueous systems comprising:
    (a) forming a core member of an electrically-conductive metal;
    (b) preparing a liquid solution containing a solvent, a semipermeable polymeric matrix material, a plasticizing agent, and DMB-DSB;
    (c) coating the core member with the liquid solution and drying the coating to form an ion-exchange membrane electrode;
    (d) in an aqueous solution containing a nonionic surfactant, adding a cation to complex with the nonionic surfactant; and
    (e) potentiometrically titrating the solution containing the complexed nonionic surfactant in an electrochemical cell containing the ion-exchange membrane electrode.

21. A process for potentiometrically titrating charged surfactants in aqueous systems comprising:
(a) forming a core member of an electrically-conductive metal;
(b) preparing a liquid solution containing a solvent, a semipermeable polymeric matrix material, a plasticizing agent, and DMB-DSB;
(c) coating the core member with the liquid solution and drying the coating to form an ion-exchange membrane electrode;
(d) potentiometrically titrating an aqueous solution containing the charged surfactant with a titrant having a charge opposite to that of the surfactant, in an electrochemical cell containing the ion-exchange membrane electrode.

* * * * *